United States Patent
Gallagher (10) Patent No.: US 9,931,267 B2
(45) Date of Patent: Apr. 3, 2018

(54) PORTABLE MAT

(71) Applicant: SweetCheeks Products, Inc., Austin, TX (US)

(72) Inventor: Ali Gallagher, Austin, TX (US)

(73) Assignee: SWEETCHEEKS PRODUCTS, INC., Austin, TX (US)

( * ) Notice: Subject to any disclaimer, the term of this patent is extended or adjusted under 35 U.S.C. 154(b) by 0 days.

(21) Appl. No.: 14/081,528

(22) Filed: Nov. 15, 2013

(65) Prior Publication Data

US 2014/0142614 A1    May 22, 2014

Related U.S. Application Data

(60) Provisional application No. 61/728,468, filed on Nov. 20, 2012.

(51) Int. Cl.
- *A61H 39/00* (2006.01)
- *A61H 7/00* (2006.01)
- *A61H 39/04* (2006.01)
- *A61B 17/132* (2006.01)

(52) U.S. Cl.
CPC .......... *A61H 7/001* (2013.01); *A61B 17/1325* (2013.01); *A61H 39/04* (2013.01); *A61H 2201/0134* (2013.01); *A61H 2201/0157* (2013.01); *A61H 2201/1284* (2013.01); *A61H 2201/164* (2013.01); *A61H 2201/168* (2013.01); *A61H 2201/1623* (2013.01); *A61H 2201/1695* (2013.01); *A61H 2203/0431* (2013.01); *A61H 2203/0456* (2013.01); *A61H 2205/081* (2013.01); *A61H 2205/086* (2013.01); *A61H 2205/108* (2013.01); *A61H 2207/00* (2013.01)

(58) Field of Classification Search
CPC .... A61B 17/1325; A61H 39/04; A61H 7/001; Y10S 5/944
USPC ....... 606/201, 204; 601/134, 138, 28; 5/653; D24/211
See application file for complete search history.

(56) References Cited

U.S. PATENT DOCUMENTS

| | | | | |
|---|---|---|---|---|
| 1,904,039 A | * | 4/1933 | Bruder | A61H 7/001 482/142 |
| 2,156,629 A | * | 5/1939 | Hutchison | A47C 7/021 297/219.1 |
| 3,744,483 A | * | 7/1973 | Picolin | A61H 7/001 4/581 |

(Continued)

FOREIGN PATENT DOCUMENTS

| CN | 201088697 | 7/2008 |
|---|---|---|
| WO | 2010141978 | 12/2010 |

OTHER PUBLICATIONS

International Search Report and Written Opinion issued for PCT Application No. PCT/US2013/070348, dated Jan. 22, 2014, 8 pages.

(Continued)

*Primary Examiner* — Diane Yabut (57) ABSTRACT

A device or system useful for temporarily reducing the appearance of cellulite and increasing local circulation, including a base with an array of protrusions having a size, shape, durometer and spacing selected to indent a user's skin under pressure. A user may position the device such that the protrusions are in contact with skin or separated from the skin by thin fabric, and then apply pressure to cause the protrusions to indent but not penetrate the skin.

25 Claims, 7 Drawing Sheets

(56) References Cited

U.S. PATENT DOCUMENTS

| | | | |
|---|---|---|---|
| 3,970,078 | A | 7/1976 | Rogers, Jr. |
| 4,086,922 | A | 5/1978 | Henderson |
| D256,841 | S * | 9/1980 | Corbett .................. D24/211 |
| 4,421,110 | A * | 12/1983 | DeLisle et al. ............ 601/134 |
| 4,614,000 | A | 9/1986 | Mayer |
| 4,673,605 | A * | 6/1987 | Sias et al. ................ 428/120 |
| D294,212 | S | 2/1988 | Sias et al. |
| 4,829,987 | A | 5/1989 | Stewart |
| 5,052,068 | A * | 10/1991 | Graebe ............... A47C 7/021 |
| | | | 297/452.23 |
| 5,134,735 | A | 8/1992 | Rose |
| 5,170,778 | A | 12/1992 | Jamis |
| 5,250,067 | A | 10/1993 | Gelfer et al. |
| 5,402,545 | A | 4/1995 | Jolley |
| D361,132 | S * | 8/1995 | Lee ........................ D24/200 |
| D369,414 | S * | 4/1996 | Lee ........................ D24/200 |
| 5,628,079 | A * | 5/1997 | Kizemchuk et al. ............ 5/653 |
| 5,639,145 | A | 6/1997 | Alderman |
| 5,820,573 | A | 10/1998 | Ramos |
| 5,938,684 | A * | 8/1999 | Lynch .................. A61H 39/04 |
| | | | 606/201 |
| 6,153,207 | A | 11/2000 | Pugliese |
| 6,443,914 | B1 | 9/2002 | Costantino |
| 6,511,445 | B2 | 1/2003 | Sivan et al. |
| 6,517,499 | B1 | 2/2003 | Pereira |
| 6,969,548 | B1 * | 11/2005 | Goldfine .................. 428/159 |
| 6,979,300 | B1 * | 12/2005 | Julian .................... A61H 7/00 |
| | | | 601/15 |
| 6,988,979 | B1 | 1/2006 | Trainor |
| D693,934 | S * | 11/2013 | Lin ........................ D24/215 |
| 8,677,532 | B2 * | 3/2014 | Legare ........................ 5/652 |
| 2002/0111574 | A1 | 8/2002 | Robbins, III et al. |
| 2004/0082890 | A1 | 4/2004 | Kuo |
| 2006/0004308 | A1 | 1/2006 | Yamauchi |
| 2006/0235345 | A1 | 10/2006 | Ivanov |
| 2006/0276731 | A1 | 12/2006 | Thiebaut et al. |
| 2008/0255599 | A1 | 10/2008 | Ide et al. |
| 2008/0262579 | A1 * | 10/2008 | Berk et al. ................ 607/104 |
| 2009/0209889 | A1 | 8/2009 | Li |
| 2010/0161014 | A1 | 6/2010 | Lynch et al. |
| 2010/0175275 | A1 | 7/2010 | Beiruti |

OTHER PUBLICATIONS

Chinese Office Action dated May 27 2016 in Chinese Application No. 201380060652.8.
English translation of Chinese Office Action dated May 27 2016 in Chinese Application No. 201380060652.8.
Supplementary European Search report dated Jun. 21, 2016 for European patent application No. 13857389.
Examination report dated Feb. 2, 2018 for corresponding Australian Patent Application No. 2013348209.
Office Action dated Dec. 13, 2017 for corresponding CN Patent Application No. 201380060652.8.

* cited by examiner

PORTABLE MAT

CROSS-REFERENCE TO RELATED APPLICATION(S)

This is a conversion of, and claims a benefit of priority from U.S. Provisional Application No. 61/728,468, filed Nov. 20, 2012, entitled "PORTABLE MAT USEFUL FOR TEMPORARILY REDUCING APPEARANCE OF CELLULITE AND INCREASING LOCAL CIRCULATION," which is fully incorporated herein by reference.

TECHNICAL FIELD

This disclosure relates generally to portable mat(s). More particularly, embodiments disclosed herein relate to a new type of portable mats suitable for use in temporarily improving local circulation, reducing the appearance of cellulite, relieving minor aches and pain, and relieving minor muscle spasms.

BACKGROUND OF THE RELATED ART

Studies have shown that a significant percentage of women and some men may have cellulite and that cellulite is genetic and may become more noticeable with age or can be affected by diet, lack of exercise, hormonal changes and/or changes in weight. Cellulite is more commonly seen in the abdomen, buttocks and thighs, but can also be seen in other parts of the body. The cellulite, under the skin, gives the skin a non-uniform appearance sometimes likened to the appearance of cottage cheese. It is a general notion that the dimpled appearance of skin due to the presence of cellulite is unbecoming.

It is understood that the appearance of cellulite can be temporarily reduced or eliminated by mechanical massage which has the effect of stimulating the local circulation to the area and promoting lymphatic drainage of excess fluids present in fat cells. Both of these effects of mechanical massage may lead to the temporary appearance of a reduction in the appearance of cellulite.

With this understanding, a number of approaches have been proposed to temporarily reduce the appearance of cellulite. For example, one approach may involve a user using creams such as those containing Caffeine or Aminophylline to temporarily reduce the appearance of cellulite. However, such creams are messy, with no immediate results (in fact, most see no reduction in the appearance of cellulite for 4 to 6 weeks with daily use), maintenance is difficult to achieve and even harder to maintain, and even when results are good, and the recurring costs can be quite expensive. Furthermore, many of the lotions and creams that are applied topically can require multiple applications per week, can require the use of drugs or chemicals, can be irritating to the skin and must be used consistently over time to achieve then maintain desirable results.

As another example, hand held therapeutic massaging devices designed to temporarily reduce the appearance of cellulite require active use and significant time requirements on the part of the user. Furthermore, undergoing such services/procedures, such as those used in endermologie or cellulaze treatments, requires the user to schedule an appointment to a specialist's office and have no 'at home' utility. Many office procedures may offer similar results in reducing the appearance of cellulite. However, these office procedures require multiple visits to a specialist's office, which are costly and usually more invasive and time consuming, all for a temporary result. In addition, the more invasive the procedure, the more technical skill required by the medical provider and the more dependent the results are on the technician. These more invasive procedures have risks of bruising, bad results and can be painful.

Example devices and methods for the reduction of cellulite can be found in the following patent documents.

U.S. Pat. No. 6,517,499 (Pereira) discloses a massage device with rotating elements. This is a hand held device complete with a suction enclosure. A reciprocating linear motion is communicated to massage applicator rollers to facilitate massaging human tissue in the treatment of cellulite.

U.S. Pat. No. 6,511,445 (Sivan et al.) is directed to a hand-held cellulite massage system with a gel dispenser. The device applies suction to an area of the body to massage that area and applies gel to treat the skin.

U.S. Pat. No. 6,443,914 (Costantino) is directed to an apparatus and method for preventing and treating cellulite. Tissues are generated or strengthened by applying radiation or an appropriate frequency to disrupt or otherwise destroy cells.

U.S. Pat. No. 5,820,573 (Ramos) is directed to a body contour massage device and method. The device consists of a rigid flat base which, when configured with contoured modules and rigid pressure nibs or blades, contours the length of an adult human body. The device operates by arranging the massage elements including buttocks, back, shoulder, and neck modules. With pressure nibs or blades to match the contoured surface of the backside of a person. The person then lies upward facing on the device with the device applied across the entire body for the desired therapeutic effect.

U.S. Pat. No. 5,402,545 (Jolley) teaches an orthopedic seat cushion for permitting free circulation and protecting the user's coccyx. A cushion with numerous protrusions is disclosed.

U.S. Pat. No. 5,628,079 (Kizemchuk et al.) is directed to a seat cushion with projections. The seat cushion has a flexible substrate and pads. The pads have a pattern of projections thereon in a spaced, parallel relationship. Here, it is indicated that the cushion provides a massage of a person's buttocks or thighs to help alleviate cellulite.

U.S. Pat. No. 5,250,067 (Gelfer et al.) is directed to a body treatment pad having a multiple number of sharpened skin-penetration protuberances. The pad includes a flexible backing sheet having a multiplicity of similarly constructed rigid blocks at spaced points along the sheet surface. Each block has at least one tapered protuberance extending away from the sheet. When the pad is held under pressure against person's body, the sharpened protuberances act as acupuncture elements to stimulate nerve endings under the skin, thereby increasing the blood circulation and relieving pain.

U.S. Pat. No. 5,170,778 (Jamis) is directed to a body massaging device which permits a user to massage his back by placing the device between his back and the flat surface.

U.S. Pat. No. 5,134,735 (Rose) is directed to a mattress cushion with multiple zones. Each of the cushion's three separate zones has a different compression modulus such that when a person presses down on the zones, support proportional to the boy's weigh is achieved.

U.S. Des. Pat. No. 294,212 (Sias et al.) is directed to a design of a seating pad having upwardly extending protuberances.

U.S. Pat. No. 4,614,000 (Mayer) is directed to patient undersheet for preventing bed sores that utilizes upwardly extending protuberances.

U.S. Pat. No. 4,086,922 (Henderson) is directed to a method and apparatus for treating cellulite containing areas of the human body. This is a hand-held device that uses a base that supports closely spaced balls. The apparatus is hand-held for massaging and kneading areas of the human body.

U.S. Pat. No. 3,970,078 (Rogers, Jr.) is directed to a hand roller massage device that is grasped by hand and uses massage rollers to massage areas of cellulite on a human body.

U.S. Pat. No. 6,988,979 (Trainor) is directed to a method of using an exercise bench for performing exercises for the reduction of cellulite which includes a textured surface on top portions of the bench.

U.S. Pat. No. 5,639,145 (Alderman) is directed to a portable, flexible, hinged cushion with material features and vibrators that can be advantageous for persons afflicted with blood circulation problems, strained muscles, etc.

U.S. Pat. No. 5,820,573 (Ramos) is directed to a massaging device with modules that fit the entire length of the human body creating a massaging effect when the user lies upward facing on the device.

U.S. Pat. No. 6,153,207 (Pugliese) is directed at a garment for treating skin through the release of chemicals bound to inside surface of the garment.

U.S. Pat. No. 4,829,987 (Stewart) is directed a method of treating the human body with a mineral solution and a body wrap to aid in the temporary reduction of cellulite.

As these examples illustrate, prior approaches to temporarily reducing the appearance of cellulite, while effective, create user compliance issues that undermine overall success, including costs, ease of use, portability, allowance for changes in the users body positioning, size of person, size of chair to accommodate placement of mat, and performance. Consequently, there is ample room for innovations and improvements.

SUMMARY OF THE DISCLOSURE

An object of the present disclosure is to provide a portable mat that can aid in the temporary reduction in the appearance of cellulite, increase of local circulation, temporary relief of minor muscle aches and pains, and relief of muscle spasm without the drawbacks existent in prior approaches mentioned above. In some embodiments, the portable mat can have one or more discrete pads. Each pad can be used by itself or with one or more pads. When in use, the portable mat provides a textured surface with protrusions for contacting an area of skin (e.g., the thighs and buttocks of a user in a seated position, the neck and/or back of a user in a resting position, etc.) which accomplishes therapeutic massage of the area with minimal to moderate movement on the part of the user and leaves the user with impressions from the textured surface on their skin which occasions the increase in local circulation to smooth the skin's surface in the post-contact period after use.

In some embodiments, a portable mat may include a base monolithically made of a thermoplastic elastomer material, having a thickness, and at least a first surface on a plane. In some embodiments, the thermoplastic elastomer material may have a thermal conductivity between 0.04-0.52 $W*m^{-1}*K^{-1}$.

In some embodiments, the base may be solid and/or have one or more openings. In some embodiments, the base may have two halves, each half of the base may be substantially a mirror image or complementary of the other half of the base. In some embodiments, the base can have a thickness between approximately 0.5 inches and approximately 0.625 inches. In some embodiments, the base may have a first thickness of approximately 0.5 inches near an edge and a second thickness of approximately 0.625 inches near the center of the base.

In some embodiments, the first surface of the base has a plurality of protrusions arranged in close proximity or adjacent to each other, forming a textured surface for the portable mat. The plurality of protrusions may have the same or similar geometric configuration, with each protrusion having a tip. In some embodiments, each protrusion may have a height between approximately 0.10 inches and 0.30 inches. In some embodiments, the plurality of protrusions may have a hardness or resilience between 10-150 Shore A on the Durometer scale. The plurality of protrusions thus configured can cause non-transdermal temporary indentation when the portable mat is in use.

Specifically, when a user uses an embodiment of a portable mat disclosed herein by sitting or resting on it, the application of the user's body weight against the portable mat's textured surface produces an effective therapeutic massage, leaving the user with an 'imprint' on the surface of their skin mirroring the textured surface of the portable mat. After a short period of time (e.g., within 15 minutes) of use, the user may feel a slight sensation of warmth. This verifiable increase in the user's skin temperature corresponds to an increase in local blood circulation caused by the user's body reacting to the portable mat's imprinting effect. After removal of the portable mat (e.g., after one half hour of use), the increased local blood circulation acts to smooth out the 'imprinted' skin surface (e.g., within an hour). The user may benefit from a temporary reduction in the appearance of cellulite in the 'massaged' area, temporary relief of minor muscle aches and pains, and/or relief of muscle spasm.

In some embodiments, the portable mat may be part of a kit which includes, for instance, a case for storing and transporting the portable mat.

Numerous other embodiments are also possible.

Embodiments disclosed herein can provide many advantages over the prior approaches mentioned above. For example, the portable mat can be used anywhere and the cost can be a fraction of that of the office procedures or the recurring cost of maintenance of other products or services. Furthermore, the effects produced by the use of a portable mat disclosed herein do not require drugs or chemicals, do not involve office visits and/or expensive device/equipment/creams/locations, and have been shown to occur immediately within one hour of use. Embodiments can be used as frequently (or infrequently) as desired. Usage can be tied to one's daily routine of sitting for thirty minutes.

These, and other, aspects of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions and/or rearrangements may be made within the scope of the disclosure without departing from the spirit thereof, and the disclosure includes all such substitutions, modifications, additions and/or rearrangements.

BRIEF DESCRIPTION OF THE DRAWINGS

The drawings accompanying and forming part of this specification are included to depict certain aspects of the disclosure. A clearer impression of the disclosure will become more readily apparent by referring to the exemplary, and therefore non-limiting, embodiments illustrated in the drawings. Wherever possible, the same reference numbers will be used throughout the drawings to refer to the same or like features (elements). The drawings are not necessarily drawn to scale.

DETAILED DESCRIPTION

Embodiments disclosed herein provide a portable mat, system, and kit that may be useful for temporarily reducing the appearance of cellulite, temporarily increasing local circulation, temporarily relieving minor muscle aches and pains, and temporarily relieving muscle spasm. Other uses may also be possible, such as relief of minor back aches or muscle spasms to the upper and lower spinal areas.

In some embodiments, the portable mat can be made of a flexible material such as thermoplastic elastomer. Other materials are also possible. For example, the portable mat can be made of rubber, plastic, glass, fiberglass, metal, bamboo, wood, hard plastic, or a composite material. As a non-limiting example, the portable mat may be made of a material having a sufficiently high durometer (e.g., 10-150 Shore A) so that the protrusions are not substantially compressed by the user's weight and can leave a visible pattern or 'imprint' on the skin after use, ensuring that the indentations they create are the intended shape and size. The portable mat has a form factor that allows it to be used in various positions such as sitting or when the user is lying on the side, on the back, or face down.

In some embodiments, a portable mat disclosed herein can be made monolithically out of a single piece of material. In some embodiments, a portable mat disclosed herein can be made using an injection molding process. In some embodiments, a portable mat disclosed herein can be non-porous and have no seams or holes. These features protect the portable mat from being penetrated by bodily fluids, dirt, chemicals, and/or high pressure water. Hence, it is easy to clean in a dishwasher.

In some embodiments, a portable mat may include one or more pads, each with a pattern of protrusions positioned thereon. In some embodiments, each of the protrusions (also referred to as protuberances) can be a three dimensional (3D) shape. As a non-limiting example, the 3D shape can be a tetrahedron or a pyramid. Other geometric 3D shapes are also possible, so long as each protrusion has a tip configured to create a desired impression in the skin and contact, but not penetrate, the skin when a person sits on the mat. These protrusions can be identical or substantially identical across all protrusions. Further, in some embodiments, the protrusions can be equally spaced from one another. In some embodiments, the protrusions can have the same height or varying heights. The number of protrusions per pad may vary from implementation to implementation, depending upon the size and/or shape of the underlying pad, as well as the size and/or shape of the individual protrusions.

A measurement of protrusions per unit area of the mat may be referred to as the protrusion density for the mat. A protrusion density may be selected such that a distance between two adjacent protrusions (e.g., as measured between their tips, edges, and/or bases) does not exceed a maximum threshold. This maximum threshold may vary depending upon individual users (e.g., age, gender, skin thickness, skin sensitivity, etc.) such that the protrusions of a portable mat can support a user's weight and that contact between the user's skin and any one protrusion does not cause damage or excessive pain to the user by that protrusion.

The protrusion density for a mat may also vary depending upon the hardness of each protrusion, the shape of each protrusion, the shape of the tip of each protrusion, and/or some other characteristic. In one embodiment, the protrusion density for a mat having pyramidal or frustro-pyramidal protrusions with a hardness of approximately 80 Shore A is between approximately 2-3 protrusions per square inch (which is an example of a unit area). However, more or fewer protrusions per square inch may be possible, depending on how much spacing is present between adjacent protrusions, the size and/or shape of the base for each protrusion, the height of each protrusion, etc. For example, a mat having rounded protrusions may have a lower protrusion density than a mat having angled protrusions, a mat with protrusions having hardness of 100 Shore A may have a higher protrusion density than a mat with protrusions having a hardness of 50 Shore A, a mat having protrusions that extend 0.5 inches may have a lower density than a mat with protrusions that extend only 0.25 inches, etc.

In some embodiments, a portable mat disclosed herein can have two or more discrete pads, each having a pattern of protrusions positioned thereon. These pads may have the same or different patterns of protrusions and may be made of the same or different materials. These pads may have the same or different shapes. In one embodiment, a portable mat can be made of two symmetrically shaped pads. In one embodiment, the pads are rectangular. Other shapes are also possible and anticipated. For example, the pads can have oval, irregular, square, circular, octagonal shapes or the like. The pads can be used separately or together at the same time. The mat size can be extended to include sufficient skin contact to effectuate a full body mat surface contact area.

The pads of a portable mat disclosed herein can be permanently or temporarily attached to each other using a variety of attachment mechanisms. For example, in one embodiment, two or more pads may be removably attached to each other via a hook and loop arrangement. As another example, in some embodiments, one or more flexible cables or cords of same or different lengths may be used to join two or more pads to form a portable mat. Other attachment mechanisms may also be possible.

The ability to separate and attach multiple pads as desired allows a user to position and/or align the pads with the contour of their individual body. For example, a user may position two pads, each under a thigh and joining at a corresponding corner to form a "V" pattern when the user sits on the mat placed on an office chair. The same user may arrange the same pads in parallel to form a "||" pattern when the user sits on the mat placed on a seat in an airplane. In this example, the airplane seat is a lot smaller and hence more restrictive than the user's office chair. However, the user can still adjust the orientation of the pads to fit the seat and the position at which it is used. The portable mat disclosed herein can therefore accommodate differences in user size, use position, seat restrictions, etc.

In some embodiments, the protrusions on a pad can taper down toward one or more sides of the pad. For example, the height of the protrusions on a pad can taper down toward a side of the pad that is designed to be positioned under the thigh just above the knee (popliteal fossa). The reduced height of the protrusions in this area can minimize pressure to the knee pit, allowing better blood circulation and lymphatic drainage and alleviating the possibility of limiting blood flow. Another example can be that the height of the protrusions on a pad can taper to the anatomical structure of the pelvis and allow for more comfort in the area of contact between the pads and the ischial spines. Another example can be that the pad itself can be constructed to be ergonomic forcing the user to tend to lean/sit in a more forward position when using the pad.

These protrusions are configured to enable a reduction in the appearance of cellulite when the skin is placed in contact with a surface of the mat patterned or otherwise textured with the protrusions for a period of time, for instance, in the range of an hour, more or less. The patterned surface promotes keeping the skin in contact with the surface relatively fixed against the surface of the mat such that fat tissue is also thus fixed relative to the textured surface. The mat can leverage a user's body weight against the textured surface as well as when there is slight movement of the body, such as shifts in the body's positioning with normal desk-type activity.

More specifically, the pattern of protrusions can be configured or otherwise arranged such that when the mat is placed under the buttocks and thighs of a user, the protrusions can impress upon the user's skin. When the mat is sat on by the user, the user's own body weight and natural motion (passive massage) can drive the protrusions into, but not breaking, the skin, pushing the fluids out from where the skin is impressed with the indentations and creating a mechanical massage. The pressure from the protrusions can also cause impressions to occur in the skin and the user's body naturally reacts by increasing blood flow to the area (erythema) to counter the indentations caused by the protrusions. The non-porous material used also enhances a warming effect and the skin temperature of the user increases during the use period. After sitting on the mat for a period of time, for instance, about half an hour, once or twice per day, the mat is separated from the user (e.g., the user stands up from sitting or lying on the mat). The indentations gradually disappear from the skin and the blood circulation to the local area begins to subside, both effects leaving an effect of temporary reduction in the appearance of cellulite.

Embodiments of a portable mat disclosed herein can have a form factor and weight comparable to a tablet computer, making them easy to carry, transport, and store. As a non-limiting example, a mat encompassing a set of two discrete pads can weigh about two pounds or less and easily accommodate carrying pads for use in a car seat, office chair, or typical sitting situations at home or at a restaurant.

Embodiments of a portable mat disclosed herein can incorporate design elements such that their actual function is not readily apparent, making it possible for users who may have concerns about revealing their purpose can carry them around without the concern that others will notice. For example, the materials can be colored using impregnating dye(s) and/or surface paint(s).

Embodiments of a portable mat disclosed herein can conform to most seating surfaces without being damaged and/or without damaging the seating surfaces.

Embodiments of a portable mat disclosed herein can be easy to clean. For example, the portable mat may be cleaned in a common household dishwasher or washed by hand. The heat of the dishwasher will not damage the integrity of the mat for repeated uses and the mat can tolerate extremes of heat, such as leaving it in the car in hot temperatures.

Embodiments of a portable mat disclosed herein can provide a low risk solution to temporarily reduce the appearance of cellulite, temporarily increase local blood circulation, temporarily relieve minor muscle aches and pains, and/or relax muscles locally. The invention and the various features and advantageous details thereof are explained more fully with reference to the non-limiting embodiments that are illustrated in the accompanying drawings and detailed in the following description. Descriptions of well-known manufacturing techniques, components and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

FIGS. 1A-1D depict top, cross-sectional, and close-up views of one embodiment of a portable mat (device 100). As depicted in one or more of FIGS. 1A-1D, device 100 may be formed with base 120 having edges with lengths L1 and L2. Base 120 may have a single thickness (e.g., T1) or base may vary in thickness and have two or more thicknesses (e.g., T2 and T3). Device 100 may be formed as a single piece, or portions of device 100 may be formed and then mechanically, chemically or thermally bonded or joined to form device 100. In one embodiment, T1 may be 0.125 inches. In one embodiment, T1 may be 0.165 inches. In one embodiment, T2 may be 0.125 inches and T3 may be 0.165 inches. Other values for T1, T2, and T3 may also be possible.

Base 120 may be formed from material selected for desired characteristics relating to use, transport, storage, or cleaning. For example, device 100 may be formed with base 120 being solid or having one or more openings (not shown) for ease of handling during use and/or transport. Device 100 may also be formed with a material having one or more characteristics including, but not limited to, anti-microbial surfaces, low thermal conductivity, flexibility, light weight, latex free, odorless, non-toxicity, color, texture, and hardness/resilience (e.g., as measured on a durometer scale).

Base 120 may be formed of flexible material based on use, transport or storage. In some embodiments, base 120 may be formed with a flexibility to conform to the user's body to ensure a maximum number of protrusions contact the user's skin, or to avoid contact with an area. For example, a user might want the maximum number of protrusions contacting the gluteus area and roll device 100 inward (i.e., may wrap device 100) around that area, or the user might want to avoid the back of the knee and may roll device 100 outward (i.e., turn out device 100) to ensure no contact with that area. In some embodiments, base 120 may be formed with a flexibility to conform to most seating surfaces without being damaged by the seating surface and without damaging the seating surface. In some embodiments, base 120 may be formed with a flexibility to enable a user to position device 100 in a desired configuration, such as for use in an airline seat, a bus seat, or the like. In some embodiments, base 120 may be formed with a flexibility to allow a user to roll device 100 for easier transport or more compact storage.

In some embodiments, base 120 may be formed from a material with a low thermal conductivity. When base 120 is in contact with human skin, low thermal conductivity may help retain heat near the skin. Retaining heat near the skin may advantageously cause local body temperatures to increase. In some embodiments, base 120 may increase local body temperatures by one degree (Fahrenheit), and may increase local body temperatures between 3-5 degrees (Fahrenheit). Increasing local body temperatures may cause blood circulation to increase in those areas.

In some embodiments, base 120 may be formed from a material that is anti-bacterial, bacteria-resistant or otherwise inhibit or decrease the likelihood of transmitting germs. In some embodiments, base 120 may be dishwasher safe to allow a user to easily clean device 100 between uses.

In some embodiments, device 100 may be formed from a polyurethane elastomer product such as PMC 780 Dry and Wet available from Smooth-On, Inc. of PA. The composition provides a nearly impervious surface, is easy to clean by hand or in a dishwasher, has a low thermal conductivity, can be formed to have a desired flexibility and hardness, does not stain, and can be formed in a variety of colors. Other materials and compositions may be possible.

Device 100 may be formed having edges 102a, 102b, 102c and 102d, with lengths L1 and L2. In one embodiment, L1 may be 13.4 inches. In one embodiment, L1 may be 13.665 inches. In one embodiment, L2 may be 8.875 inches. In one embodiment, L2 may be 9.29 inches. In some embodiments, at least one edge has a length L1 or L2 between 10-24 inches. Other values for L1 and L2 may also be possible.

Edges of device 100 may be straight or curved. At least one edge may have length L1 or L2 to allow a person to sit on device 100 and have substantially all of the person's buttocks or thighs supported by device 100.

Figure 1A:
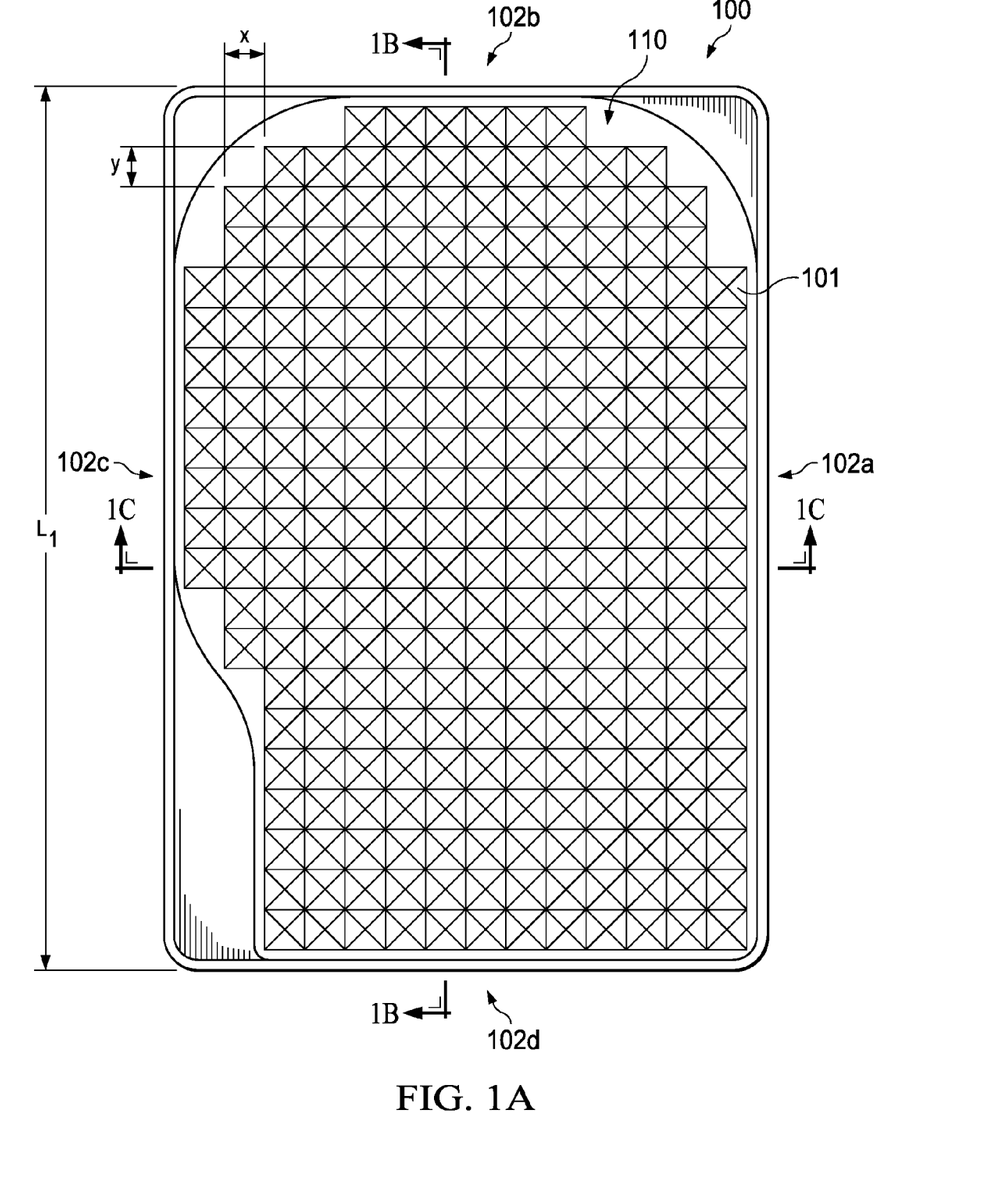
FIGS. 1A-1D depict top, cross-sectional, and close-up views of one embodiment of a portable mat.
Figure 1B:
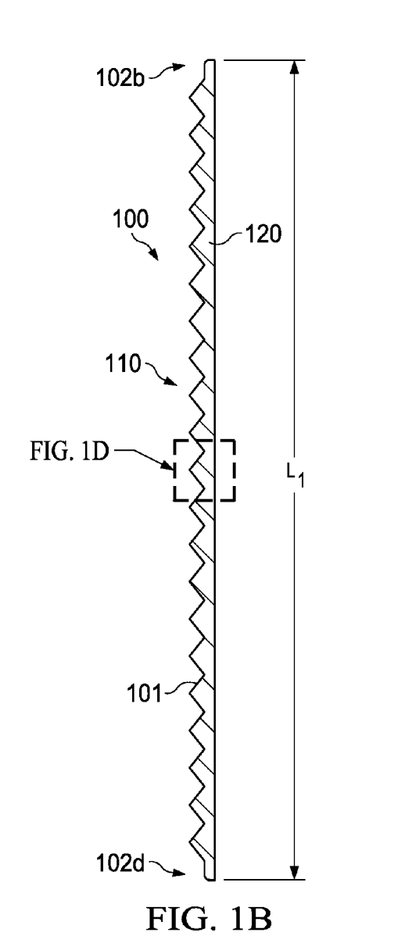
Figure 1C:
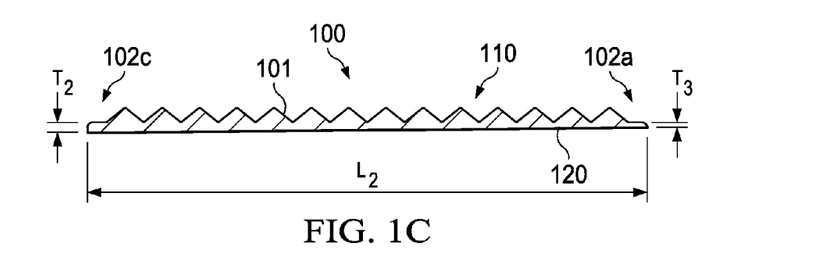
Figure 1D:
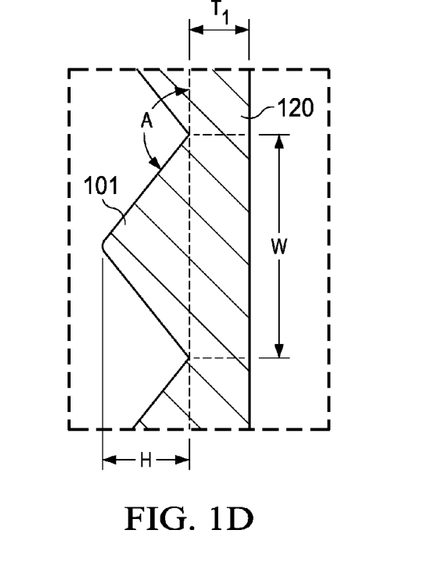

Device 100 may be formed with base 120 having array 110 of protrusions 101 protruding from a top or first surface lying on a plane of base 120. Each protrusion 101 may have a geometric configuration with an angular surface, such as a pyramid, or may have a curved surface, such as a cone. Protrusions 101 may be formed having surfaces with varying slopes. In some embodiments, each protrusion 101 may be formed with a blunt (not sharp) tip or point. A blunt tip may be formed with a first slope near the base and a second slope that is less steep than the first slope near the tip. For example, a first slope may equate to a 45 degree angle, and a second slope may equate to a 30 degree angle. A pyramidal frustum and a conical frustum are examples in which the second slope may be substantially zero. As illustrated in FIG. 1D, each protrusion 101 may be defined by a width W, a height H, and an angle A relative to the top side of base 120. In some embodiments, H may be between 0.265 and 0.259 inches. In some embodiments, W may be between 0.5 and 0.75 inches. In some embodiments, A may be between 120-150 degrees. In some embodiments, width W may correspond to width X or width Y such that protrusions 101 contact other protrusions.

Protrusions 101 may be formed with a particular hardness that can be measured using a durometer. A durometer measures the hardness of a material. In this case, hardness may be defined as a material's resistance to permanent indentation. The durometer scale is typically used as a measure of hardness in polymers, elastomers, and rubbers. One or more of the height H, width W, angle A or hardness may be selected such that, in use, the tip of any protrusion 101 may leave an indentation or impression in a user's skin but protrusions 101 do not pierce, penetrate or otherwise cause permanent damage to the skin. In some embodiments, protrusions 101 may have between 10-150 Shore A hardness on the durometer scale.

Protrusions 101 may be formed as part of array 110. In some embodiments, array 110 may be formed having columns and rows. The number of protrusions 101 in any row or column may vary. For example, as depicted in FIG. 1A, array 110 may be shaped to have a desired appearance, and protrusions 101 may be positioned and spaced accordingly. The number of protrusions 101 in array 110 may vary based on the size, spacing and shape of protrusions 101. Array 110 may be formed with protrusions 101 proximate other protrusions 101. In some embodiments, protrusions 101 may contact other protrusions 101.

Figure 2:
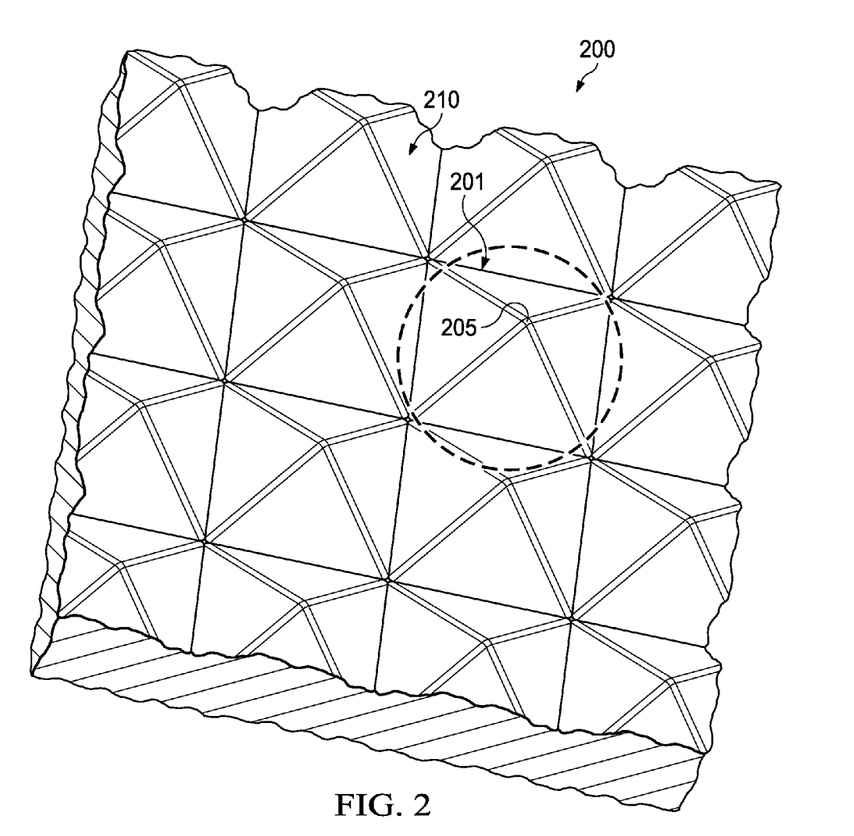
FIG. 2 depicts a close-up perspective view of a portion of one embodiment of a portable mat.

FIG. 2 depicts a close-up perspective view of a portion of one embodiment of a portable mat (device 200). Device 200 may have array 210 of protrusions 201. Array 210 of protrusions 201 may be an embodiment of array 110 of protrusions 101 described above. Like protrusions, protrusions 201 may be shaped, sized, and spaced to meet desirable anatomical or physiological differences in soft tissues. These differences may allow protrusions 201 to force or otherwise cause fluid to go out of soft tissues, increase blood circulation in the area, cause irritation to inhibit or discourage fluid from building up in soft tissues, or provide some other physiological difference resulting in a decreased appearance of cellulite in the area.

Array 210 may comprise columns and rows of protrusions 201. Each protrusion 201 may be close to other protrusions 201 in array 210 or may contact other protrusions 201 in array 210. Each protrusion 201 may have blunt tip or point 205 shaped and sized to prevent damage to skin. As used herein, the term "tip" may refer to a portion of protrusions 201 configured for non-transdermal, non-penetration contact with skin. Tips 205 of protrusions 201 may be sized and shaped to cause indentations in skin after contact with the skin, but do not damage nerves, blood vessels, lymph nodes, bones, or other tissues. Embodiments may prevent or avoid damage to the skin such as nerve damage, a buildup of scar tissue, and the like. For example, tips 205 or protrusions 201 may be shaped, spaced and sized such that a user may sit on or otherwise contact skin with device 200 for a period of time (e.g., 5 minutes, 10 minutes, 30 minutes, etc.) and the pressure will cause protrusions 201 to leave indentations in the skin, but the indentations smooth out and disappear within a short time period (e.g., 5-45 minutes) after device 200 is disengaged from contacting the skin. Those skilled in the art will appreciate that the size, shape and spacing of indentations will be affected by other factors which may include, but are not limited to, the person's weight, gender, body type, absence or degree of appreciable cellulite and age.

Figure 3:
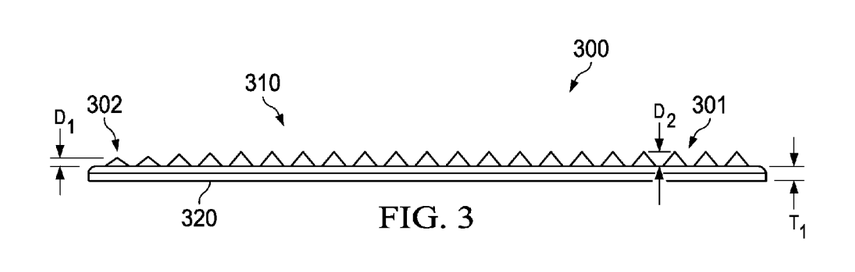
FIG. 3 depicts a side view of one embodiment of a portable mat.

FIG. 3 depicts a side view of one embodiment of a portable mat (device 300), illustrating different configurations of protrusions on a base. Device 300 may be an embodiment of device 100 described above. In this example, base 320 may have a thickness that remains substantially constant across base 320, but profiles of protrusions on base 320 may vary across base 320. As depicted in FIG. 3, base 320 may have a first thickness T1, and protrusions 301 may vary in size (e.g., height) from a first edge to a second edge opposite the first edge, from a first edge to an area near the middle, or some combination. For example, in one embodiment, the height of array 310 of protrusions on device 300 can taper down toward a first edge such that D1 for protrusion 302 is less than D2 for protrusion 301. Advantageously, this taper or reduction in height may allow device 300 to be used under the thigh with the tapered portion proximal to the knee. The reduced height of protrusions 301 in this area can minimize pressure to tissues in the knee pit, allowing better blood circulation and lymphatic drainage and alleviating the possibility of limiting blood flow.

Figure 4:
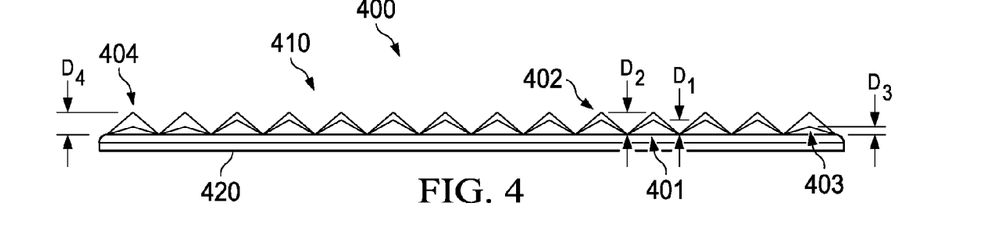
FIG. 4 depicts another side view of one embodiment of a portable mat.

FIG. 4 depicts another side view of one embodiment of a portable mat (device 400). Device 400 may be an embodiment of device 300 depicted in FIG. 3, rotated 90 degrees. As illustrated in FIG. 4, array 410 of protrusions may span from a first edge to a second edge opposite the first edge. The protrusions may vary in height between two edges, as exemplified by D3 and D4. Combined with the example shown in FIG. 3 in which the protrusions may also vary in height (D1 and D2) between two edges, FIG. 4 shows an example embodiment in which array 410 of protrusions may vary in height toward the edges, as illustrated by protrusions 401, 402, 403, and 404. Those skilled in the art will appreciate that D1, D2, D3 and D4 may differ from implementation to implementation as needed and/or desired.

Figure 5:
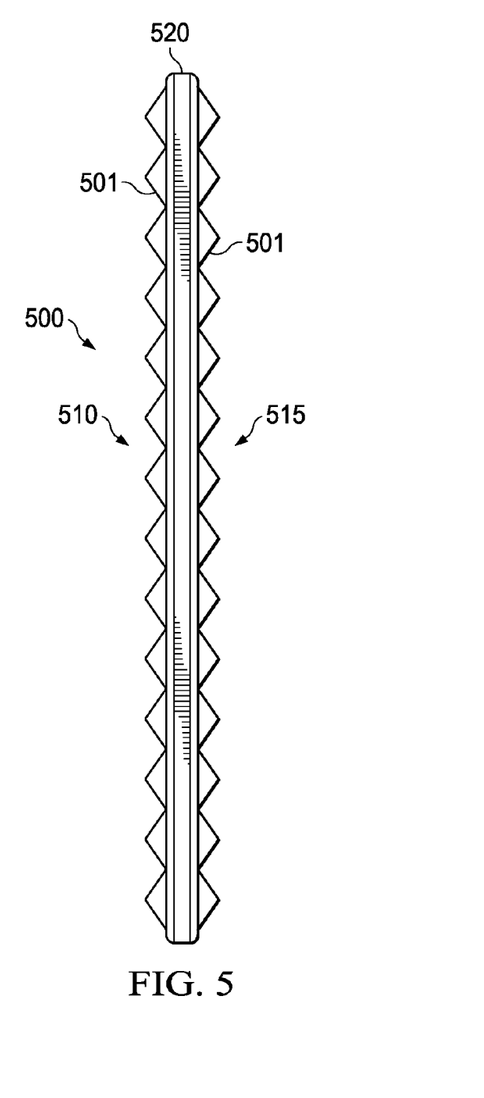
FIGS. 5 and 6 depict side views of embodiments of a portable mat.
Figure 6:
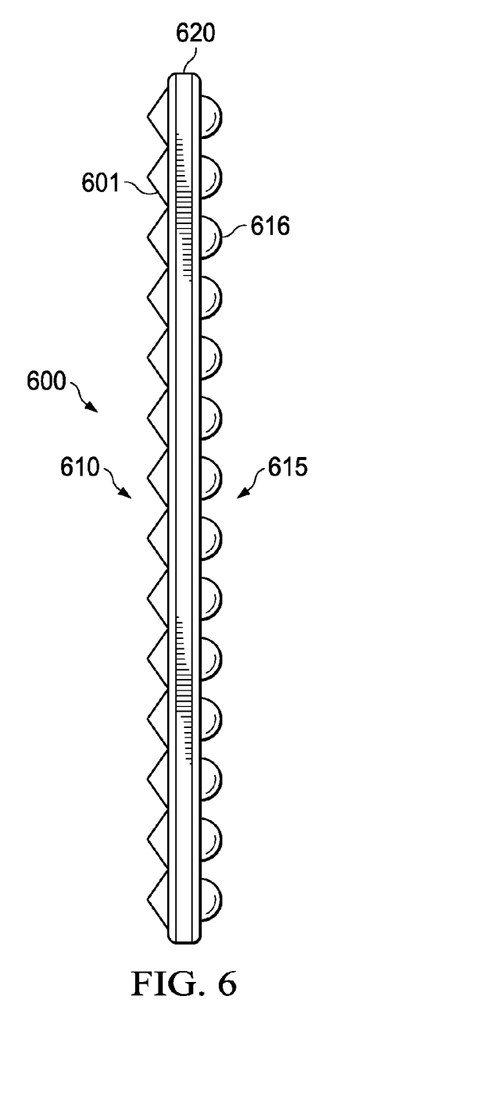

FIGS. 5 and 6 depict side views of embodiments of a portable mat. As depicted in FIG. 5, device 500 may include base 520 having array 510 of protrusions 501 protruding from a first side of base 520 and array 515 of protrusions 501 protruding from a second side of base 520. As depicted in FIG. 6, device 600 may include base 620 having array 610 of protrusions 601 protruding from a first side of base 620 and array 615 of protrusions 616 protruding from a second side of base 620.

As exemplified in FIG. 6, protrusions 601 may be angular, such as pyramidal, and protrusions 616 may be curved, such as semi-spherical, or otherwise have a shape that is different than protrusions 601. Advantageously, having two sides with each side having protrusions with different shapes, hardness, sizes, etc., may allow a user to control and/or choose effects of device 600. For example, a user may tolerate sitting on a first side for a longer amount of time, a user may like the results associated with one side rather than the other side, or some other reason.

Figure 7:
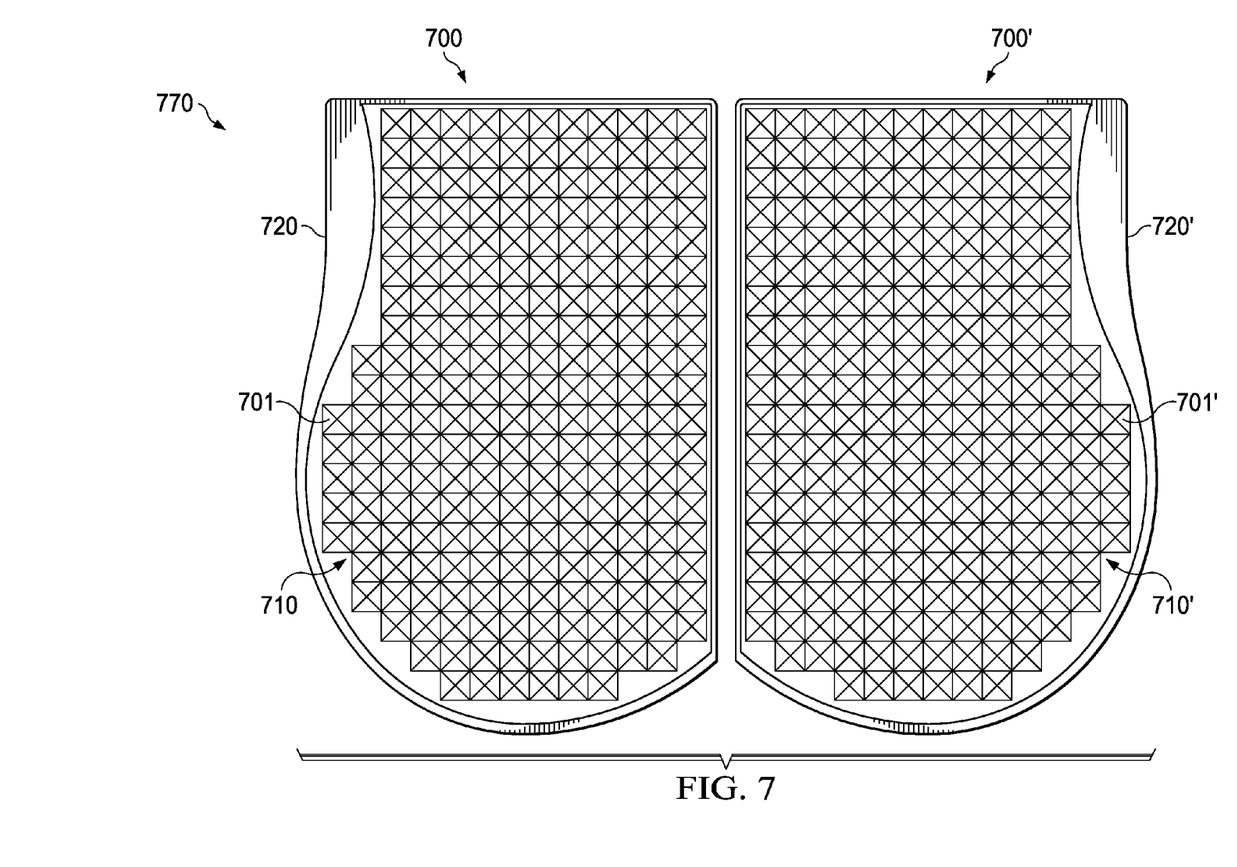
FIGS. 7-9 depict top views of various embodiments of a portable mat system.
Figure 8:
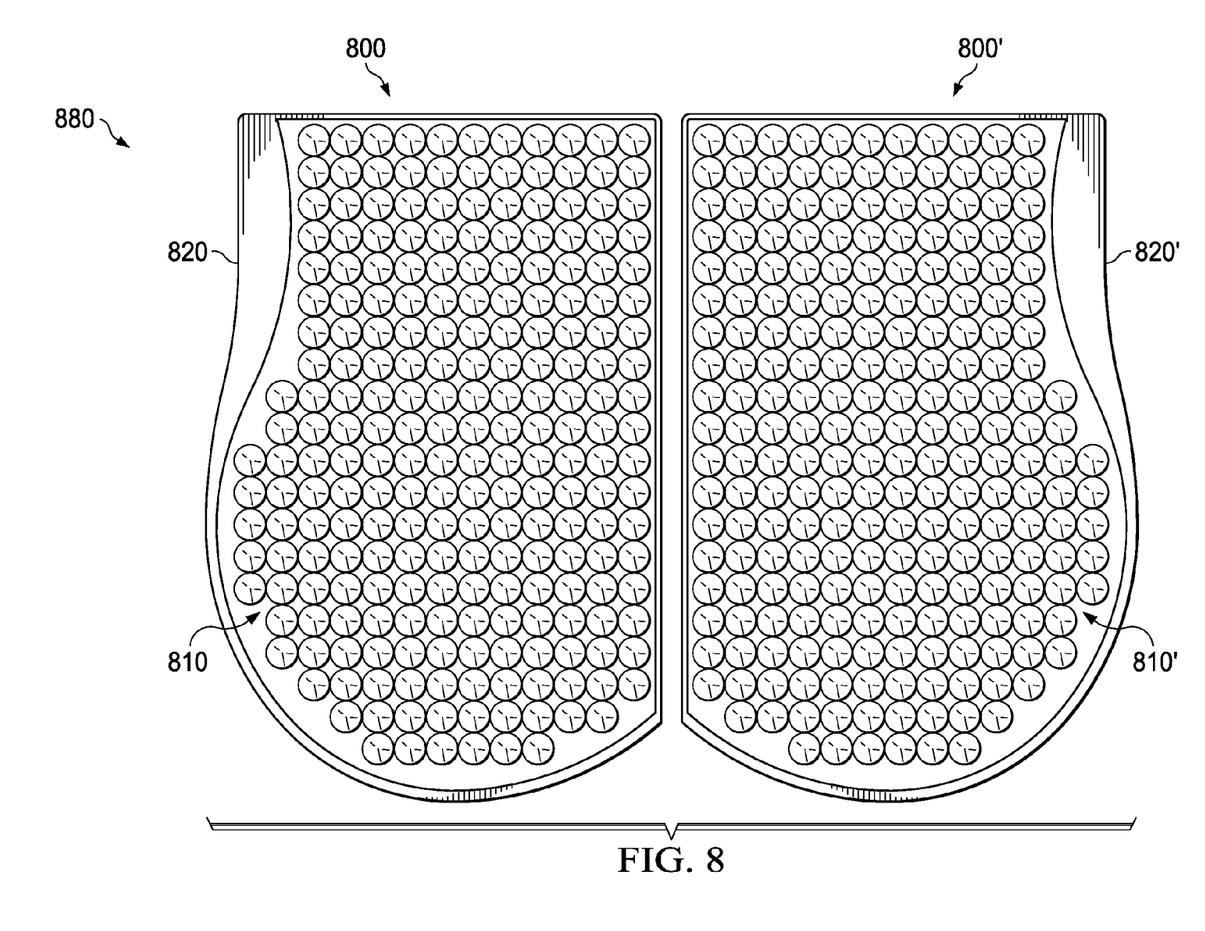
Figure 9:
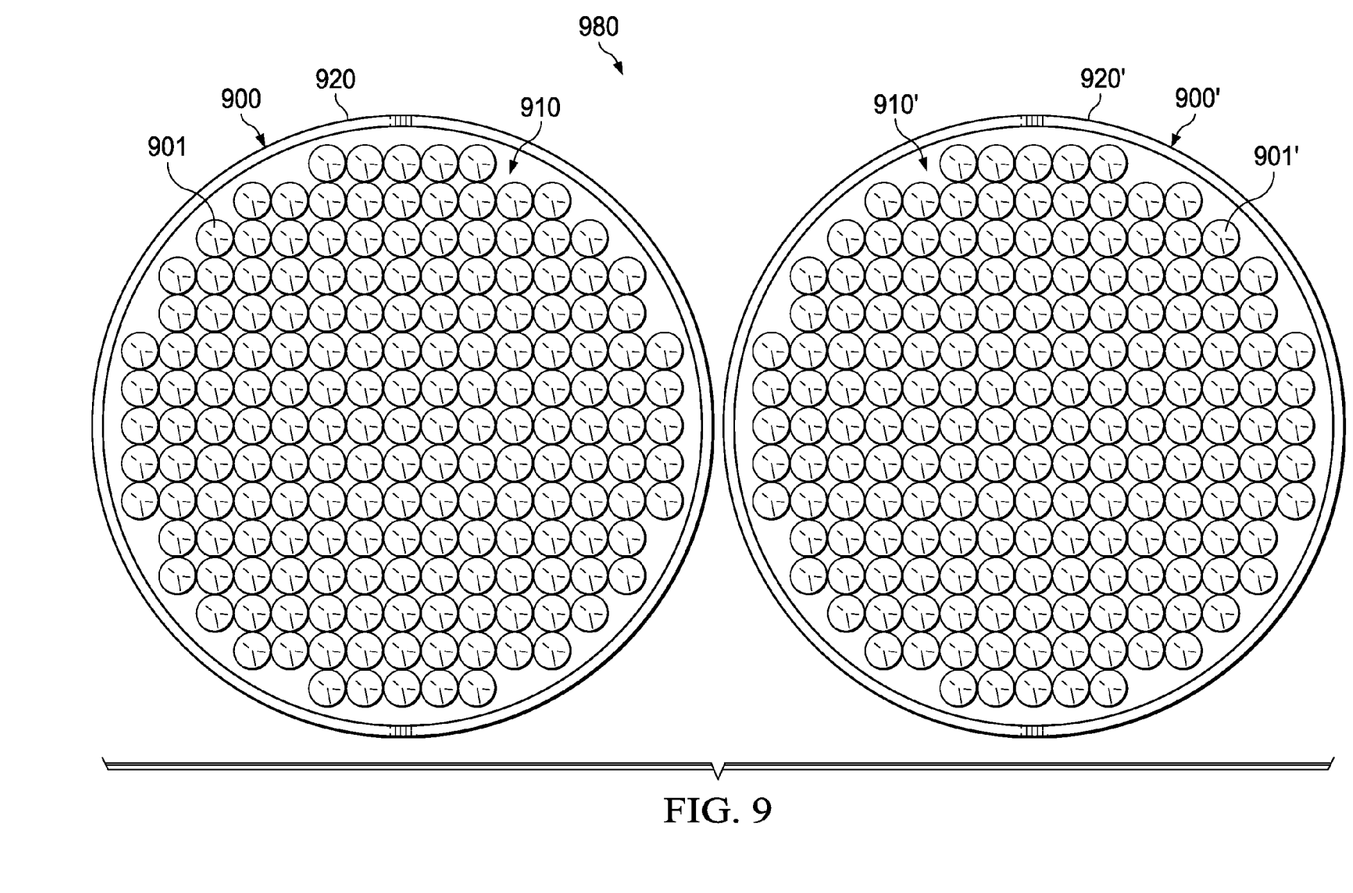

FIGS. 7-9 depict top views of various embodiments of a portable mat system. Specifically, system 770 may include two halves 700, 700'. Each half 700, 700' may have array 710, 710' of pointed protrusions 701, 701'. As depicted in FIG. 7, halves 700, 700' may be symmetric. In some embodiments, halves 700, 700' may be complementary, identical, asymmetric, or mirrored. Halves 700, 700' may be shaped to maximize the number of protrusions 701, 701' in contact with the thighs or buttocks of a seated user. As depicted in FIG. 7, halves 700, 700' may have a first edge that is substantially straight and a second edge that has a curvature based on a profile of a user's buttocks and thighs. Having an edge that is substantially straight allows a user to position halves 700, 700' in a "V" or "||" configuration in which both halves 700, 700' are positioned relative to a single limb of a user to treat a greater surface area of the limb, or in which both halves 700, 700' are positioned on the outside of each thigh or buttock. Having an edge that is curved may allow a user to conform each half 700, 700' to optimize contact with protrusions 701, 701' or to avoid contact with protrusions 701, 701'. System 770 may form part of a kit (not shown), which may also include a carrying case, cleaning materials, belts or straps to assist a user in positioning system 770 or retaining system 770 in a desired position, or other tools.

FIG. 8 depicts one embodiment of system 880 having two halves 800, 800'. Each half 800, 800' may have array 810, 810' of cone shaped protrusions 801, 801'. As depicted in FIG. 8, halves 800, 800' may be symmetric and each may have an elongated shape such as oval or rectangular. Other shapes for the base of a portable mat may also be possible. In some embodiments, halves 800, 800' may be complementary, identical, asymmetric, or mirrored. Halves 800, 800' may be shaped to maximize the number of protrusions 801, 801' in contact with the thighs or buttocks of a seated user. As depicted in FIG. 8, halves 800, 800' may have a first edge that is substantially straight and a second edge that has a curvature based on a profile of a user's buttocks and thighs. Having an edge that is substantially straight allows a user to position halves 800, 800' in a "V" or modified "V" configuration in which both halves 800, 800' are positioned relative to a single limb of a user to treat a greater surface area of the limb, or in which both halves 800, 800' are positioned on the outside of each thigh or buttock. Having an edge that is curved may allow a user to conform each half 800, 800' to optimize contact with protrusions 801, 801' or to avoid contact with protrusions 801, 801'. System 880 may form part of a kit (not shown), which may also include a carrying case, cleaning materials, belts or straps to assist a user in positioning system 880 or retaining system 880 in a desired position, or other tools.

Embodiments may include other variations as well. FIG. 9 depicts one embodiment of system 980 having bases 920, 920', each of which may constitute half of a kit (not shown). Base 920, 920' may have array 910, 910' of pointed protrusions 901, 901'. As depicted in FIG. 9, base 920, 920' may be circular, and pointed protrusions 901 may be semispherical, angular, or conical. Those skilled in the art will appreciate that other shapes or combinations of shapes may also be possible.

In some embodiments, devices and systems described above may be attached together for transport or storage. In some embodiments, devices and systems may attach together for transport, storage or use. A connection between two devices, bases, etc., may include a fixed connection, a hinged connection, or some other form of connection. A connection may be permanent, or devices, bases, etc., may be connected and separated as desired. Advantageously, the ability to separate components or modify configurations may allow embodiments to treat people having various body types, weights, etc.

These, and other, aspects of the disclosure and various features and advantageous details thereof are explained more fully with reference to the exemplary, and therefore non-limiting, embodiments illustrated and described herein. It should be understood, however, that the detailed description and the specific examples, while indicating some embodiments, are given by way of illustration only and not by way of limitation. For example, in some embodiments, a portable mat may have two pads of the same or similar shape and size attached along a length of the mat such that the pads can fold up to form a carrying case for items, including but not limited to a laptop, paperwork, or magazines. As another example, in some embodiments, a portable mat may have two halves connected with a flexible material that allows the two halves to be placed in various but limited arrangements and distances in relation to each other.

Furthermore, descriptions of known materials and manufacturing techniques may be omitted so as not to unnecessarily obscure the disclosure in detail. Various substitutions, modifications, additions and/or rearrangements within the spirit and/or scope of the underlying inventive concept will become apparent to those skilled in the art from this disclosure.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the accompanying appendices, a term preceded by "a" or "an" (and "the" when antecedent basis is "a" or "an") includes both singular and plural of such term, unless clearly indicated otherwise (i.e., that the reference "a" or "an" clearly indicates only the singular or only the plural). Also, as used in the description herein and in the accompanying appendices, the meaning of "in" includes "in" and "on" unless the context clearly dictates otherwise. The scope of the present disclosure should be determined by the following claims and their legal equivalents.

What is claimed is:

1. A mat, configured for causing non-transdermal temporary indentation in the flesh of a user by concentrating pressure on localized points on the flesh during low energy, sustained contact when the mat is in use, comprising:
a base monolithically comprising a thermoplastic elastomeric material, the base further comprising at least a first surface on a plane of the base; and
a plurality of protrusions, each of the plurality of protrusions consisting of a square pyramid shape, each edge between triangular side faces of said square pyramid shape being beveled, said plurality of protrusions protruding from the first surface of the base in the direction of intended contact with the flesh of the user, each of the plurality of protrusions contiguous with at least one other of the plurality of protrusions on the first surface of the base, wherein each of the plurality of protrusions comprises a blunt tip, wherein the beveled edges are each uniformly beveled from said first surface to said tip.

2. The mat of claim 1, wherein the base is solid.

3. The mat of claim 1, wherein the base has one or more openings.

4. The mat of claim 1, wherein the base has a thickness between approximately 0.5 inches and approximately 0.625 inches and said plurality of protrusions are exposed for contact with the flesh of the user.

5. The mat of claim 1, wherein the base has a first thickness at a first outermost edge of the base and a second thickness at an opposed second outermost edge of the base, the second thickness being greater than the first thickness.

6. The mat of claim 1, wherein the protrusions of the plurality of protrusions have a height that tapers from a first height at a first edge of the base to a second height at a second edge of the base, the first height being greater than the second height.

7. The mat of claim 1, wherein each protrusion of the plurality of protrusions has a height between approximately 0.10 inches and 0.30 inches.

8. The mat of claim 1, wherein the thermoplastic elastomeric material has a hardness of between 10-150 Shore A on a durometer scale.

9. The mat of claim 1, wherein the thermoplastic elastomeric material has a thermal conductivity between approximately 0.04-0.52 $W*m^{-1}*K^{-1}$.

10. The mat of claim 1, further comprising a plurality of pointed protrusions protruding from a second surface of the base.

11. The mat of claim 1, wherein the base has different thicknesses at opposed outermost edges.

12. The mat of claim 1, further comprising a plurality of opposed protrusions protruding from an opposed, second surface of said base, each of said plurality of opposed protrusions being semi-spherical in shape.

13. A system configured for causing non-transdermal temporary indentation in the flesh of a user by concentrating pressure on localized points on the flesh during low energy, sustained contact when in use, the system comprising:
a set of bases, each base of the set of bases monolithically comprising a thermoplastic elastomeric material, the base further comprising:
at least a first surface on a plane of the base; and
a plurality of protrusions, each of the plurality of protrusions consisting of a square pyramid shape, each edge between triangular side faces of said square pyramid shape being beveled, said plurality of protrusions protruding from the first surface of the base in the direction of intended contact with the flesh of the user, each of the plurality of protrusions contiguous with at least one other of the plurality of protrusions on the first surface of the base, wherein each of the plurality of protrusions comprises a blunt tip,
wherein the beveled edges are each uniformly beveled from said first surface to said tip.

14. The system of claim 13, wherein the set of bases comprises two halves, wherein each half is complementary of the other half.

15. The system of claim 13, wherein the set of bases comprises two halves and each said half is substantially a mirror image of the other half.

16. The system of claim 13, wherein each base of the set of bases has a thickness between approximately 0.5 inches and approximately 0.625 inches, the base has different thicknesses at opposed outermost edges and said plurality of protrusions are exposed for contact with the flesh of the user.

17. The system of claim 13, wherein the protrusions of the plurality of protrusions have a height that tapers from a first height at a first edge of the base to a second height at a second edge of the base, the first height being greater than the second height, each said protrusion having a height between approximately 0.10 inches and 0.30 inches.

18. The system of claim 13, wherein the thermoplastic elastomeric material has a hardness of between 10-150 Shore A on a durometer scale.

19. The system of claim 13, wherein the thermoplastic elastomeric material has a thermal conductivity between approximately 0.04-0.52 $W*m^{-1}*K^{-1}$.

20. The system as in claim 13, wherein each base is defined by and bounded by two straight edges intersecting orthogonally and a curvilinear edge joining the two straight edges.

21. The system of claim 13, wherein the edges of each protrusion of the plurality of protrusions each have a first slope near the base and a second, lesser slope, near the blunt tip.

22. A kit configured for causing non-transdermal temporary indentation in the flesh of a user by concentrating pressure on localized points on the flesh during low energy, sustained contact when in use, the kit comprising:
- at least one base, each base of the at least one base comprising:
  - at least a first surface on a plane of the base; and
  - a plurality of protrusions, each of the plurality of protrusions consisting of a square pyramid shape having each edge between triangular side faces of said square pyramid shape being beveled, protruding from the first surface of the base in the direction of intended contact with the flesh of the user, each of the plurality of protrusions contiguous with at least one other of the plurality of protrusions on the first surface of the base, wherein each of the plurality of protrusions comprises a blunt tip, wherein the beveled edges are each uniformly beveled from said first surface to said tip; and
- a case for storing and transporting the at least one base.

23. The kit of claim 22, wherein the base is monolithically made of a thermoplastic elastomeric material.

24. The kit as in claim 23, wherein the set of bases comprises two halves, each half being substantially a mirror image of the other half, each half defined by and bounded by two straight edges intersecting orthogonally and a curvilinear edge joining the two straight edges, and wherein the protrusions of the plurality of protrusions have a height that tapers from a first height at a first edge of the base to a second height at the second edge of the base, the first height being greater than the second height.

25. The kit of claim 22, wherein each protrusion of the plurality of protrusions has a height between approximately 0.10 inches and 0.30 inches.

* * * * *